United States Patent [19]
Garrison

[11] Patent Number: 5,601,576
[45] Date of Patent: Feb. 11, 1997

[54] SURGICAL KNOT PUSHER AND METHOD OF USE

[75] Inventor: Michi E. Garrison, Belmont, Calif.

[73] Assignee: Heartport Inc., Redwood City, Calif.

[21] Appl. No.: 288,674

[22] Filed: Aug. 10, 1994

[51] Int. Cl.⁶ .................................................... A61B 17/04
[52] U.S. Cl. ............................................ 606/148; 606/139
[58] Field of Search .................................. 606/139, 148; 289/17

[56] References Cited

U.S. PATENT DOCUMENTS

| | | | |
|---|---|---|---|
| 5,334,200 | 8/1994 | Johnson | 606/139 |
| 5,397,326 | 3/1995 | Mangum | 606/148 |
| 5,403,330 | 4/1995 | Tuason | 606/148 |

*Primary Examiner*—Gary Jackson
*Attorney, Agent, or Firm*—Townsend and Townsend and Crew LLP

[57] ABSTRACT

A surgical knot pusher device is described which has a knot pushing head mounted on the distal end of an elongated rod. The head of the device has a smoothly radiused knot pushing surface on the leading edge with two symmetrical suture paths which curve smoothly away from the knot pushing surface. The suture rests in a shallow groove which has a wall on either side to keep the suture in the groove. Near the leading edge of the pushing head the walls of the groove are lower so that the knot can be pushed directly against the tissue being sutured. On one side of the knot pushing head, there is a single eyelet in the path of one of the suture ends. The eyelet is made so that the suture can be easily threaded through the eyelet with the curved needle which is on the end of the suture without any need to remove the needle. Preferably, at least the head of the device is made from polysulfone or another suitable plastic material. A method for tying knots in surgical sutures using the surgical knot pusher device is described with special reference to using the device and method for endoscopic surgery. The surgical knot pusher device is especially well adapted for tying sutures in a new procedure for closed chest mitral valve replacement surgery. A method of using the surgical knot pusher device for tying knots in sutures to secure a valve prosthesis in place during closed chest mitral valve replacement surgery is described.

32 Claims, 10 Drawing Sheets

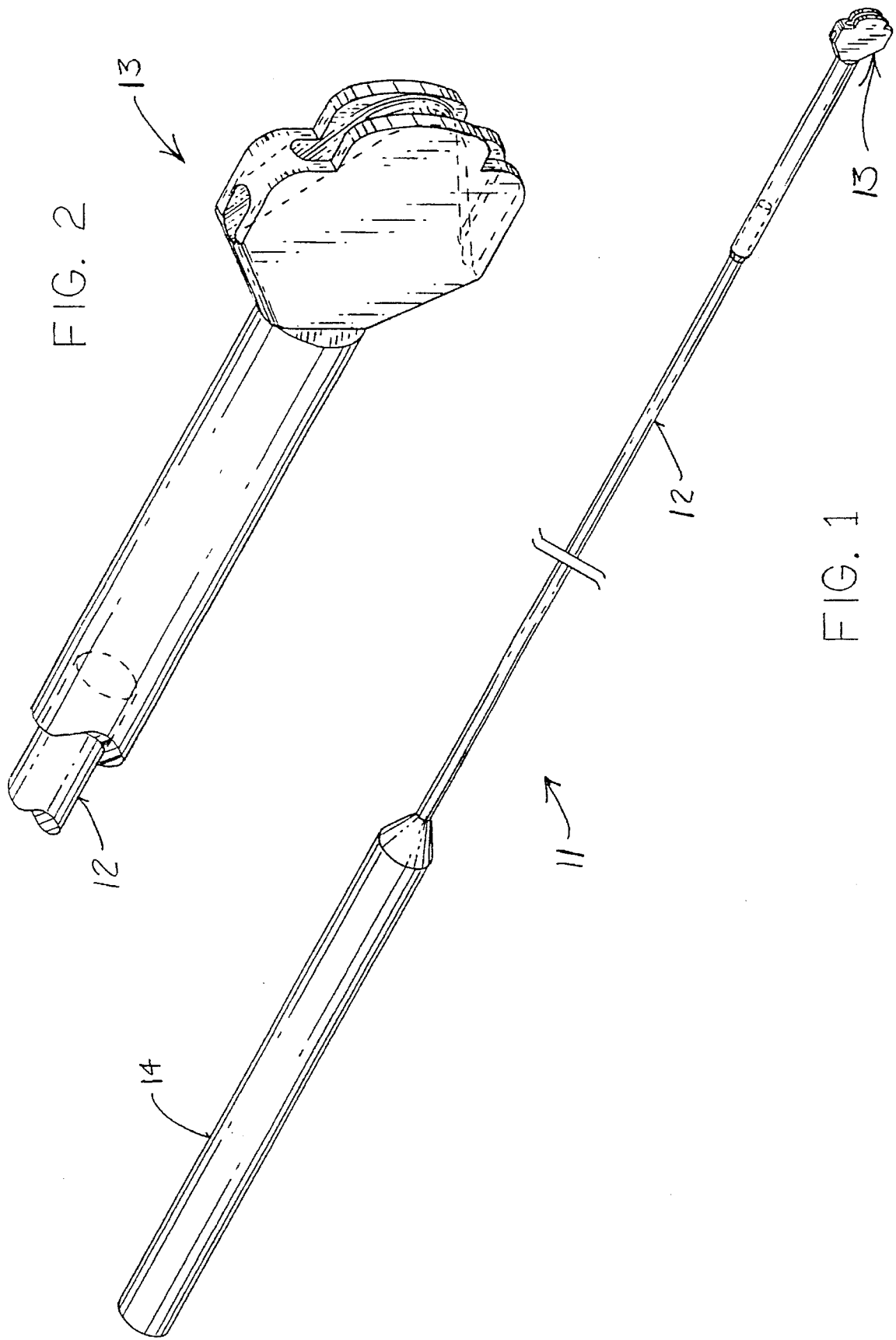

SURGICAL KNOT PUSHER AND METHOD OF USE

FIELD OF INVENTION

The present invention relates to a device to facilitate the tying of surgical sutures at remote sites within the body during endoscopic surgery and other minimally invasive surgical procedures. A method for tying surgical sutures and a method for tying surgical sutures in closed chest mitral valve replacement surgery are also presented.

BACKGROUND OF THE INVENTION

Minimally invasive surgical techniques have emerged as an important trend within the field of surgery. Minimally invasive surgery differs from standard open surgery in that surgical procedures are performed through small incisions in the body under the guidance of endoscopy, fluoroscopy, ultrasound or other remote imaging techniques. Minimally invasive surgical techniques reduce the morbidity of surgical procedures and greatly accelerate patient recovery. In many cases minimally invasive surgical techniques also reduce the overall cost of surgery, especially by shortening the recovery period during which patients must stay in the hospital. The speedy recovery reduces the financial burden of surgery on the patients by allowing them to resume their normal lives and their work more quickly. The widespread adoption of minimally invasive surgical techniques results in tremendous benefits not only for the individual patients, but also for society as a whole.

Many established surgical procedures have been converted from open surgical techniques to minimally invasive surgical techniques. One of the earliest procedures to benefit from this trend was arthroscopic knee surgery. The benefits of arthroscopic surgery to the patient in terms of decreased morbidity and faster recovery were at once evident and the procedure was quickly adopted, almost entirely replacing open surgery for diagnosis of knee injuries and meniscectomy or removal of torn cartilage. As the instruments and techniques for arthroscopic surgery improved, more complex procedures, such as repair of torn ligaments and tendons, also became possible.

Many other surgical procedures for both diagnostic and therapeutic purposes have been converted to minimally invasive surgical techniques through the use of endoscopes. One of the most recent procedures that has been successfully converted to minimally invasive surgical techniques by use of the laparoscope is cholecystectomy or gallbladder removal.

One of the great challenges facing minimally invasive surgery is the advancement of minimally invasive surgical techniques into the area of cardiac surgery. Certain cardiac surgery procedures that previously were only possible through open chest surgery have already been converted to minimally invasive surgical techniques. For example, catheter techniques have been developed for occlusion of patent ductus arteriosus or atrial septal defects and for valvuloplasty of stenotic aortic or mitral valves. Instruments and techniques have also been developed for endoscopic approaches to the heart, allowing more complex cardiac surgical procedures to be performed through minimally invasive surgical techniques. One such procedure that could benefit from minimally invasive surgical techniques is the replacement of a stenotic or insufficient mitral valve. Several techniques for closed chest mitral valve replacement surgery are described in co-pending patent application, Ser. No.08/163,241, filed Dec. 6, 1993, the complete disclosure of which is incorporate herein by reference.

One of the important challenges in minimally invasive surgical techniques is that of placing sutures in the tissue at the operating site and applying properly tied suture knots through the narrow access of an endoscopic cannula or other equally restrictive access passage. Two different approaches are commonly used in tying sutures in endoscopic surgery. These can be classified generally as intracorporeal knot tying techniques for tying sutures at the surgical site within the body and extracorporeal knot tying techniques which allow knots to be tied in the sutures outside of the body then transferred to the surgical site using a knot pusher.

Intracorporeal knot tying can be performed using endoscopic graspers or forceps to manipulate the sutures in a technique similar to instrumented knot tying in conventional surgery. Alternatively, specialized intracorporeal knot tiers can be used. Various intracorporeal knot tiers are shown in U.S. Pat. Nos. 5,234,443 to Phan et al., 4,641,652 to Hutterer et al. and 5,281,236 to Bagnato et al. Tying sutures using a graspers or an intracorporeal knot tier is difficult and tedious compared with standard bimanual methods of surgical knot tying. Using intracorporeal knot tiers usually requires specialized training in operating the instrument and, even in the hands of the most skilled operators, usually requires more time than standard knot tying techniques. In procedures where few knots have to be tied, where access to the surgical site is difficult or where the length of the procedure is not critical, intracorporeal knot tying may be the method of choice.

However, for closed chest mitral valve replacement, the complexity and time consumption of using intracorporeal knot tying techniques can be prohibitive. Surgical replacement of a diseased mitral valve can involve tying up to twenty individual multiple-throw suture knots, with up to 4 to 5 throws per suture. The rate of post surgical complications in cardiac procedures rises proportionally to the length of time that the patient must spend on cardiopulmonary bypass. Therefore, it is extremely important to keep the duration of the procedure as short as possible.

Experienced surgeons can be very deft at standard bimanual methods of surgical knot tying. In time-sensitive procedures it is best to take advantage of this practiced and well honed knot tying skill, rather than to try to retrain the surgeon to use complex intracorporeal knot tying techniques. Some knot pushers are designed specifically to take advantage of this prior skill by allowing the surgeon to form the suture knots extracorporeally, then use the knot pusher to transfer the knots to the surgical site and tighten them in place. A well designed knot pusher allows the surgeon to use a knot tying technique that closely mimics the standard bimanual knot tying technique and does not add undue complication to the procedure.

A common type of surgical knot pusher is made with a C-shaped loop on the distal end of an elongated shaft, as exemplified in U.S. Pat. No. 3,871,379 to Clarke. The opening of the C faces distally from the shaft and the opening is sized to pass the desired size of suture. These devices are used by first passing the suture through the tissue to be tied and bringing both ends of the suture out through the surgical entry point so that a knot can be tied extracorporeally. The C-shaped loop is then placed over the knot and is used to slide the knot down the suture to the surgical site. The knot may then be tightened by pulling on the suture ends. This type of knot pusher has several disadvantages. The knot pusher must be reloaded onto the suture thread each time another throw is added to the suture knot. This adds time and complexity to the tying technique. In many cases, the orientation of the C-shaped loop on the knot pusher prevents the knot from being pushed directly up to the tissue that is to be sutured. This can leave a bit of slack in the suture that would be a severe problem in valve replacement surgery because it could cause the replacement valve to loosen and potentially displace from its proper position in the heart or could lead to perivalvar leaks. The open gap of the C-shaped loop can accidentally drop the suture while pushing the knot down if it is not carefully handled. This can be very frustrating to the surgeon because the knot pusher will have to be rethreaded, which is much more difficult once the knot is halfway down the suture and within the body cavity. Also, the knot pusher has no means to insure that the knot remains centered on the knot pusher. The surgeon must carefully maintain equal tension on both ends of the suture or the knot will slide sideways out of the C-shaped loop. While this type of knot pusher works well with monofilament sutures, it has been found to be ineffective and difficult to use for braided sutures which are the type often preferred for valve replacement surgery. This is due to the fact that the narrow knot pushing edge within the C-shaped loop places too much pressure against the knot, which tends to make the knot lock up rather than sliding along the suture.

Another type of knot pusher has a pair of opposing grooves on the head of the knot pusher with a flat surface between them. Examples of this type of knot pusher can be seen in U.S. Pat. Nos. 5,234,444 to Christoudias and 5,217,471 to Burkhart. The flat surface between the grooves allows the device to push the knot directly against the tissue that is being sutured and it separates the two ends of the suture so that the tension to tighten the knot acts parallel to the tissue surface, which more effectively tightens the knot than pulling the sutures perpendicular to the tissue surface. However, these knot pushers have the disadvantages that they must be reloaded onto the suture every time another throw is added to the knot and they are even more prone to dropping knots than the devices previously described.

A number of surgical knot pushers have been designed to overcome the problem of dropping the knot while transporting it to the surgical site. In general, this type of knot pusher has a pair of eyelets on opposite sides of the head of the device. Examples of this type of knot pusher can be seen in U.S. Pat. Nos. 5,176,691 to Pierce and 5,192,287 to Fournier. The two eyelets are very effective at avoiding dropping the knot and at keeping the knot properly centered in front of the device. The disadvantage of having two eyelets is that it makes it more difficult to thread the device onto the ends of the sutures. In addition, each time another throw is added to the knot, at least one end of the suture must be unthreaded from the eyelet, then rethreaded after the knot is made. This adds undue time and complexity to the knot tying procedure.

A few devices have been made with a single eyelet or passage through the head of the knot pusher. Examples of these can be found in U.S. Pat. Nos. 4,602,635 to Mulhollan et al., 5,292,327 to Dodd et al., 5,282,809 to Kammerer et al. and 5,217,470 to Weston. Invariably, this type of knot pusher has asymmetrical paths for the two ends of the suture, which results in uneven tension on the suture at the knot. The preferred suture knot for securing a replacement heart valve, which is a series of square knots, cannot be properly tied unless the two ends of the suture can be pulled with even tension. Therefore, this type of single eyelet knot pusher is not well suited for suturing replacement heart valves and is more useful for procedures that call for a slip knot, such as a fisherman's knot, Roeder knot, multiple half hitches or another type of suture knot that can be applied asymmetrically.

One interesting variation of the single eyelet knot pusher can be seen in U.S. Pat. No. 5,269,791 to Mayzels et al. In order to make the device easier to thread onto the suture, the eyelet has been replaced with a tapered metal spiral. The last turn of the spiral is made with a diameter larger than the suture material, but smaller than a knot in the same suture. The suture is loaded onto the knot pusher by placing the suture into the proximal turn of the spiral and winding it around the device until the suture is in the center of the spiral. The present inventor has found that this technique is not easy to practice in a surgical setting and that the device is not immune from dropping or tangling knots.

It should be noted that another subgenre of knot pushers, sometimes referred to as an endo loop, is made to deliver a pretied ligation loop to a remote surgical site. An example of such a device can be seen in U.S. Pat. No. 5,242,459 to Buelna. Because these devices deliver a closed loop of suture material, they are only useful for ligating vessels and, then, only when the vessel has already been severed. They cannot be used for ligating a vessel before it is severed or for approximating tissues. Therefore, they would be of little use in mitral valve replacement surgery.

Another common type of surgical knot pusher is exemplified in U.S. Pat. No. 5,257,637 to El Gazayerli. This knot pusher has a pair of opposing jaws very much like a pair of endoscopic forceps. The jaws have slots on their distal ends and one of the jaws pivots relative to the other. When the jaws are closed, the slotted ends can be used to push a knot through a cannula or a lumen in an endoscope. Once the jaws exit the distal end of the cannula, they can be separated. This effectively makes the head of the knot pusher wider so that, when the ends of the sutures are pulled, the tension on the knot is applied parallel to the tissue surface, which is more effective for tightening the knot. This device is most useful when a wider knot pusher is desired, but the only access to the surgical site is through a narrow cannula or other narrow opening. However, this type of knot pusher is difficult to use because it must be reloaded onto the suture every time another throw is added to the knot. As it is described in the patent, only one jaw of this knot pusher pivots, so the paths of the two ends of the suture are somewhat asymmetrical when the jaws are open. A later improvement to this device, not described in the patent, solves this problem by making both jaws of the knot pusher pivot symmetrically.

In general, the above-described existing knot pusher devices have been found to be suitable for advancing knots that are tied in braided suture material, which is significant because the preferred suture material for mitral valve replacement surgery is braided nylon, dacron or polyester sutures. This is due to the fact that, in each of these devices, the paths of the sutures through the device include corners or other abrupt changes in direction that cause significant amounts of friction as the knot is advanced. Monofilament sutures are smoother so there is less friction between the suture strands or between the strands and the knot pusher. Monofilament sutures are also relatively stiffer than braided sutures of the same size, so they tend to round out the corners in the suture path through the device. Braided sutures, on the other hand, have a rougher surface texture which causes more friction between the suture strands and against the device. Also, because the more flexible braided sutures conform to every curve in the path, they are more sensitive to corners or other abrupt changes in direction.

When a badly placed corner in a knot pusher presses against a knot in a braided suture, it tends to lock the knot so that it will not slide. This jams the knot pusher, slowing down the procedure and frustrating the surgeon.

Another detail of construction that is significant in mitral valve replacement surgery is that, when the replacement valve used is a mechanical valve as opposed to a bioprosthesis, the knot pusher must be made so that no metal parts can possibly come in contact with the mechanical replacement valve. This is because mechanical heart valves are made with highly polished surfaces that may also be coated with a hemocompatible coating such as pyrolytic carbon to reduce hemolysis and platelet attachment. Any disturbance in the surface of the valve or the coating could become a locus for increased hemolysis, thrombogenisis or platelet attachment and thrombosis. This could lead to possibly fatal post-surgical complications. Thus, at least the leading edge of the knot pusher should be made of plastic or another material that will not damage the surface of the replacement valve if there is accidental contact between them during installation. Many of the prior art knot pushing devices are impractical for constructing out of plastic because of their complex geometries or a need for high strength in the moving parts. Therefore, they would not be suitable for use in valve replacement surgery.

SUMMARY OF THE INVENTION

In keeping with the foregoing discussion, a general objective of the present invention is to provide a surgical knot pusher suitable for use in endoscopic surgery and other minimally invasive surgical techniques. A particular objective is to provide a surgical knot pusher which is optimized for use in the new surgical technique of closed chest mitral valve replacement.

The surgical knot pusher should facilitate a knot tying technique which closely mimics the standard bimanual suture tying technique used in open surgery. The knot pusher should also be easy to thread onto the ends of the suture. It should not need to be rethreaded for every additional throw of a surgical knot so that multiple-throw surgical knots can be formed quickly and easily. The knot pusher should be highly resistant to dropping a knot while transporting it to the surgical site and it should not require being completely withdrawn in order to pick up a knot in the unlikely event that one slips off of the knot pusher during use. The knot pusher should allow the knot to be pushed directly against the tissue or material being sutured so that there is no slack left in the suture that could cause complications.

The knot pusher should be well adapted for forming symmetrical knots such as surgeons' knots, square knots and reef knots, which are preferred for mitral valve replacement surgery. This requires that the paths for the two ends of the suture material through the knot pusher should be symmetrical. It also requires that tension on the ends of the suture material should be translated to the knot as a tension that is parallel to the surface of the tissue being sutured, as is necessary for proper tightening of these types of knots. A closely related aspect of these objectives is that the knot pusher should be well adapted for the use of braided suture materials. This requires that the paths of the suture ends through the knot pusher should be smooth and continuous without corners or abrupt changes in direction as the path of the sutures goes from parallel to the tissue surface to perpendicular to it. There should not be an undue amount of pressure placed directly on the knot that might cause it to lock up and jam the knot pusher.

In order that the knot pusher be usable with mechanical heart valves, as well as bioprosthetic valves, the design of the knot pusher should be well suited for construction out of plastic or other materials compatible with the fragile hemocompatible coatings that are used on mechanical heart valves.

In accordance with these objectives, in a preferred embodiment, the present invention takes the form of a surgical knot pusher device which has a knot pushing head mounted on the distal end of an elongated rod. The elongated rod may optionally be made with a handle on the proximal end. The head of the device has a smoothly radiused knot pushing surface on the leading edge. The symmetrical paths of the two suture ends curve smoothly away from the leading edge of the pushing surface so that there are no abrupt turns in the path of the suture. The smoothly curving suture path rests in a shallow groove which has a wall on either side to keep the suture in the groove. Near the leading edge of the pushing head the walls of the groove are lower so that the knot can be pushed directly against the tissue being sutured. On one side of the knot pushing head, there is a single eyelet in the path of one of the suture ends. The eyelet is made so that the suture can be easily threaded through the eyelet with the curved needle which is on the end of the suture without any need to remove the needle. Preferably, at least the head of the device is made from polysulfone or another suitable plastic material.

The surgical knot pusher of the present invention provides one of the essential instruments for facilitating closed chest mitral valve replacement. In the closed chest mitral valve replacement procedure, the left atrium of the heart is accessed through a specially designed cannula in the right side of the chest. The mitral valve is located under endoscopic and/or direct visualization. In some cases, the leaflets of the diseased valve are removed. Using a needle holder introduced through the cannula, multiple individual mattress sutures are placed around the annulus of the mitral valve with the ends of the sutures extending outside of the body through the cannula. The sutures are placed through the suture ring of the replacement valve and the valve is advanced along the sutures until it is seated against the annulus. At this point, the knot pusher is used to tie the sutures to secure the valve in place. The two ends of a suture are located and one end of the suture is threaded through the eyelet of the knot pusher. The second end of the suture is thrown around the first end to form an overhand knot and the knot pusher is used to advance the knot along the sutures until the knot is tight against the suture ring of the valve. The knot pusher is withdrawn until the head of the device is outside of the body, then a second overhand knot is thrown in the opposite sense to the first knot. The second knot is advanced until it is against the first knot so that a square knot is formed. A series of 4 to 6 throws are made in the suture and the ends of the suture are cut off. Then, this process is repeated for each of the sutures through the annulus. Thus, the device and method of the present invention provide a quick and efficient means for forming secure knots in sutures during the closed chest mitral valve replacement procedure. Other objects and advantages of the invention will no doubt occur to those skilled in the art upon reading and understanding the following detailed description along with the accompanying drawings.

BRIEF DESCRIPTION OF THE DRAWINGS

FIG. 1 shows a front view, partially in cross section of the surgical knot pusher of the present invention.

FIG. 2 shows a side view of the surgical knot pusher of FIG. 1.

DETAILED DESCRIPTION OF THE INVENTION

Figure 3C:
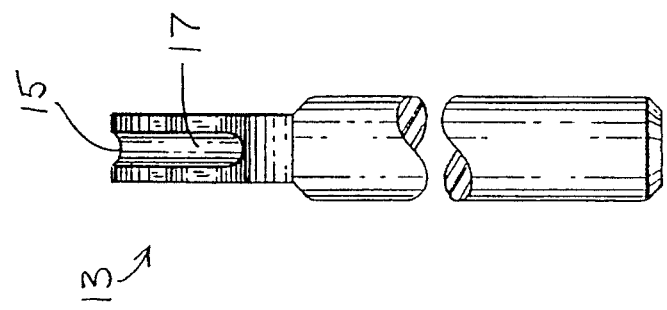
FIGS. 3 A–D show left side, right side and top view, respectively, of the head of the surgical knot pusher of FIG. 1.

A preferred embodiment of the surgical knot pushing device 11 of the present invention can be seen in FIGS. 1 and 2. The knot pushing device 11 has a knot pushing head 13 mounted on the distal end of an elongated shaft 12. The length of the shaft 12 in the illustrated preferred embodiment is approximately 25 cm. In other preferred embodiments, the shaft 12 can be anywhere from 15–35 cm in length or longer if required. The elongated shaft 12 should be made of a rigid material, such as stainless steel. Other rigid materials, such as other metals, rigid plastics or reinforced plastics would also be suitable materials for the elongated shaft 12. For easier handling, the proximal end of the elongated shaft 12 is made with an attached handle 14. The handle 14 can be made integrally of the same material as the elongated shaft 12 or a separate handle made of metal or plastic can be affixed to the shaft. Alternatively, the proximal end of the elongated shaft 12 can be made with a knurled surface to provided a non-slip gripping surface or it can be made without any handle. The knot pushing head 13 may be permanently affixed to the shaft 12 or the head 13 may be detachable from the shaft 12 by threads or other detachable means of coupling. By appropriate selection of materials, the entire device 11 can be made disposable for a single use only or the device can be made resterilizable for multiple uses or disposable detachable heads 13 could be supplied for use with a resterilizable handle 14 and shaft 12. If desired, the head, the shaft and the handle can all be made integrally of the same material.

The knot pushing head 13 is shown in greater detail in FIGS. 3 A–D. FIG. 3A shows a left side view of the knot pushing head 13, 3B shows a front view, 3C a left side view and 3D a top view from the distal end of the device. The knot pushing head 13 is preferably made of a plastic material so that it will not damage the highly polished surface or the hemocompatible coating on a mechanical heart valve. The selection criteria for suitable plastic materials are that it should be a rigid plastic so that it maintains the knot pushing head geometry, low coefficient of friction for smooth advancement of knots by the device, biocompatible and compatible with common sterilization methods, including high temperature flash steam sterilization if the device is to be reusable. The first choice of materials for the knot pushing head 13 is polysulfone because of its ability to withstand repeated steam sterilizations. Other suitable materials that have been contemplated for the knot pushing head 13 include Teflon®, polyetherimide and polycarbonate. If the entire device 11 or the knot pushing head 13 is intended to be supplied presterilized for single use only, this eases the requirement for compatibility with steam sterilization, thereby increasing the number of candidate materials. In this case other plastic materials such as polypropylene, high density polyethylene or polystyrene may be used for the knot pushing head.

In an alternate embodiment of the device, intended for uses other than installation of mechanical heart valves, the knot pushing head 13 can be made of metal, such as stainless steel or titanium or cobalt alloys. This alternate embodiment would be suitable for installation of bioprosthetic heart valves, such as porcine or cadaver heart valves, or for a multitude of other surgical procedures.

The leading edge of the knot pushing head 13 is made with a smoothly radiused knot pushing surface 15. The radius of the knot pushing surface 15 of the preferred embodiment illustrated in FIG. 3B is approximately 2 mm. There is quite a range of effective radii allowable for the knot pushing surface 15. At a minimum, the radius should be approximately 2–3 times the size of the knot in the suture material being used; the maximum radius of the knot pushing surface 15 is limited only by the practical size limits of the device. The illustrated embodiment of the invention is made with the largest dimension of the knot pushing head 13 less than 11 mm so that the device will easily fit through an oval cannula that is specially design for closed chest mitral valve replacement surgery. Other commonly used endoscopic cannulæ have internal lumens of 12 mm, 10 mm and 5 mm. The internal lumen size of the cannula used, or the size of the incision if no cannula is used, determines the maximum dimension of the knot pushing head and, therefore, the maximum allowable radius of the knot pushing surface 15. The smoothly radiused knot pushing surface 15 provides a number of advantages. It avoids putting undue pressure directly on the knot that could cause the knot to bind as it is pushed forward. It also separates the two ends of the suture and directs the tension on the suture ends so that it is applied parallel to the surface of the tissue being sutured so that the knot will tighten properly when tension is applied to the suture ends.

The paths 16, 17 for the two ends of the suture are substantially symmetrical on the left and the right side of the knot pushing head 13. In the illustrated embodiment, the curve of the knot pushing surface 15 subtends an angle of approximately 60 degrees. The paths 16, 17 of the two suture ends continue tangentially from the curved knot pushing surface 15 at the ends of the 60 degree arc so that there are no corners or abrupt changes of direction in the suture paths 16, 17.

Alternatively, the knot pushing surface 15 can be made with other geometries, as long as they exhibit the important characteristics of a convexly curved leading edge and a smoothly curved transition for the suture paths 16, 17. For example, one alternative would be a 180 degree circular arc with a diameter just slightly smaller than the internal diameter of the cannula the device must pass through. Another alternative would be a knot pushing surface 15 with an elliptically curved arc. Other types of simple and compound curved arcs would also be acceptable.

Figure 3D:
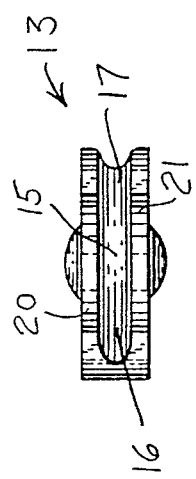
Figure 3B:
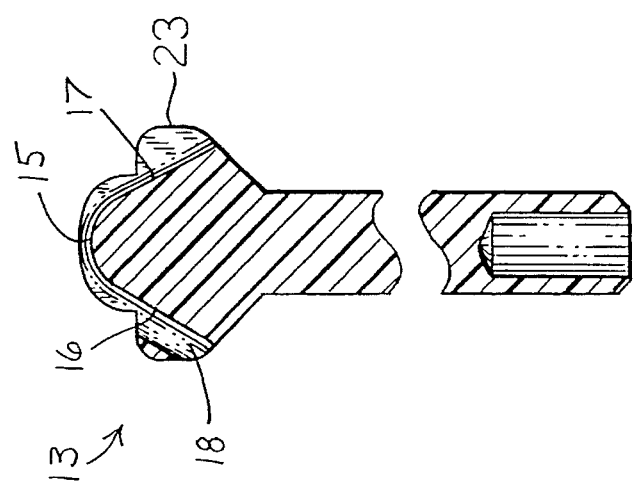
Figure 3A:
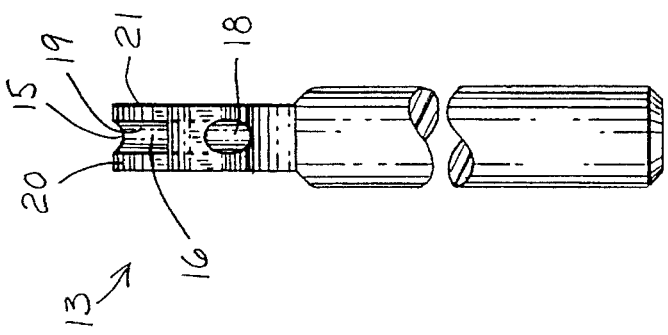
Figure 4A:
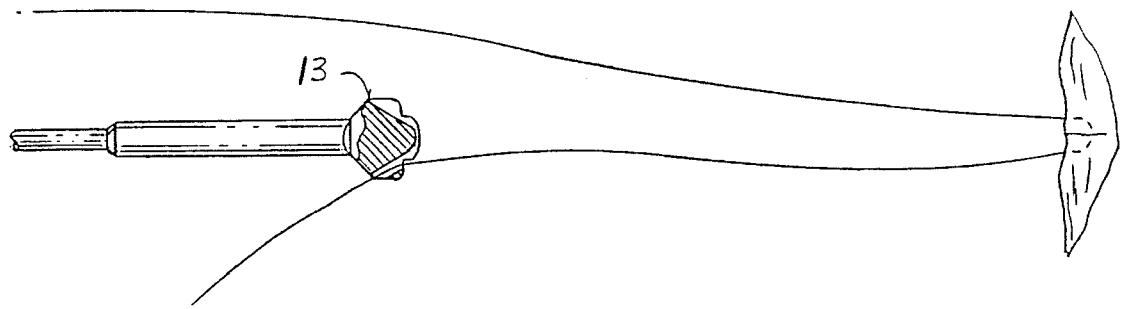
FIGS. 4 A–F show the operation of the surgical knot pusher used for tying a knot in a suture.
Figure 4B:
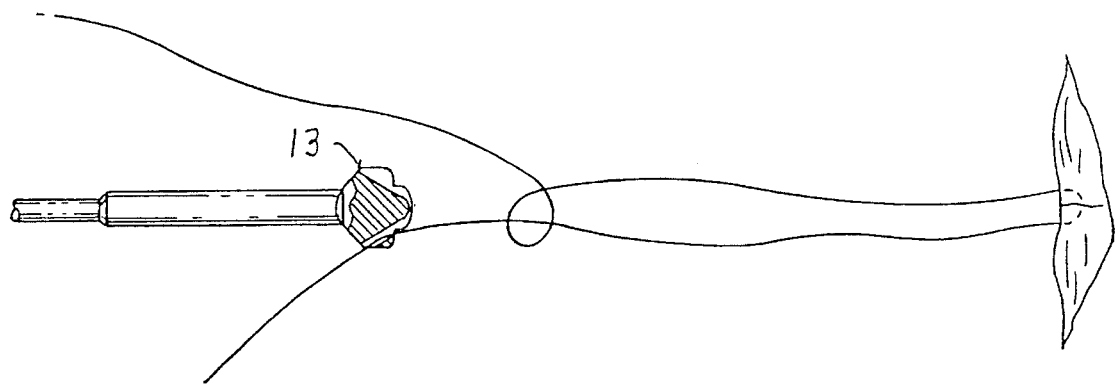
Figure 4C:
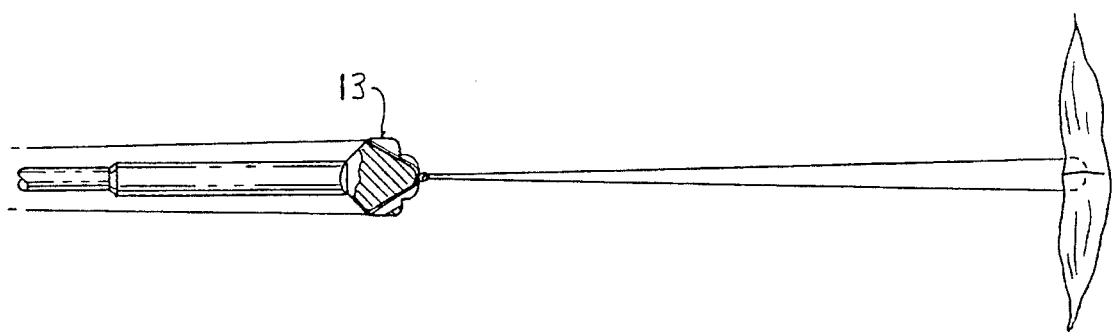
Figure 4D:
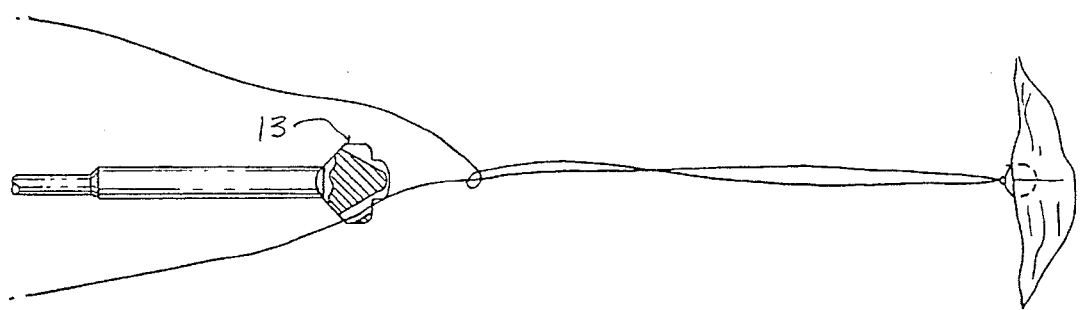
Figure 4E:
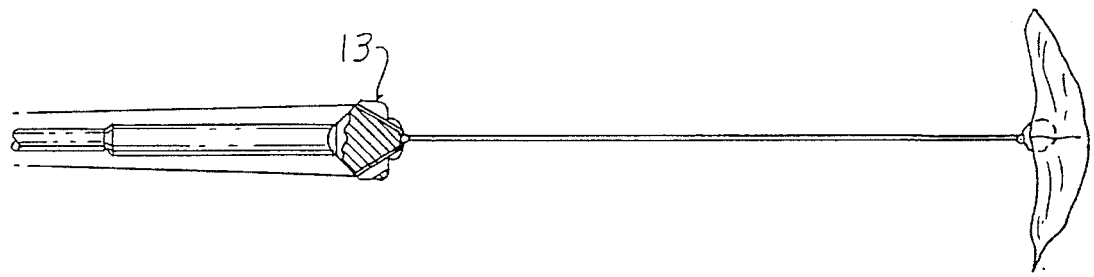
Figure 4F:
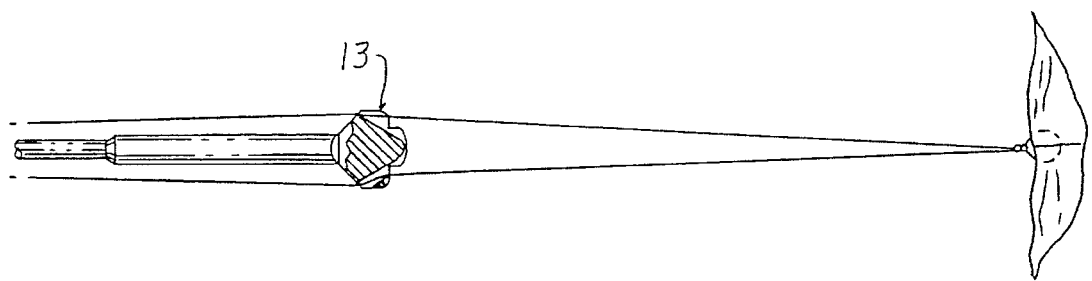

As can be seen in FIGS. 3A, 3C and 3D, the curved knot pushing surface 15 and the rest of the suture paths 16, 17 lie in a shallow groove 19 along the leading edge of the knot pushing head 13. This groove 19 is bordered by two walls 20, 21 to keep the suture in the groove 19. The groove 19 is shallowest right at the distal tip of the knot pushing head 13 so that walls 20, 21 do not prevent the knot from being pushed directly against the tissue being sutured. The walls 20, 21 are slightly higher along the rest of the suture paths 16, 17 to effectively keep the suture material in the groove 19.

On one side of the knot pushing head 13, there is a single eyelet 18 along the path 16 of the suture. One end of the suture passes through the eyelet 18. The single eyelet 18 effectively prevents the knot pusher 11 from dropping knots as they are transported to the surgical site, but it does not interfere with the knot tying technique, which will be explained in more detail below. Preferably, the eyelet 18 is dimensioned so that the suture material can be easily threaded through the eyelet 18 with a curved suture needle still attached to the end of the suture material. Unlike prior art surgical knot pushers or knot tiers that have a single eyelet, the two paths 16, 17 of the suture ends are symmetrical as they pass through the knot pushing head 13. This makes the present invention much better suited for forming symmetrical knots, such as surgeons' knots and square knots or reef knots, because the two ends of the suture material are tightened evenly.

In the preferred embodiment illustrated, the single eyelet 18 is a fully closed loop. In other preferred embodiments, the eyelet 18 could be made with a slot in it or be made of a helix of wire to allow quick loading of the suture into the eyelet 18 without having to thread the end of the suture through the eyelet 18.

On the opposite side of the knot pushing head 13, diametrically opposed to the eyelet 18, the walls 21 of the groove 19 are made somewhat higher to form an open suture guide 23 along the suture path 17. The open suture guide 23 serves to keep the suture within the suture path 17, but does not interfere with the knot tying technique, as described below.

In the left and right side views in FIGS. 3A and 3C, it can be seen that the knot pushing head 13 of the device is much narrower in the direction perpendicular to the groove 19. This is advantageous because space is usually at a premium at the surgical site in endoscopic surgery. With this geometry, the knot pushing head 13 takes up considerably less of the limited space available than the round headed knot pushers that are shown in the prior art. The shape also makes it easier for the surgeon to align the device properly with the ends of the suture under endoscopic visualization. When the wider major axis of the knot pushing head 13 is visually aligned with the suture where it passes through the tissue, the knot pusher 11 is properly aligned for tightening the knot. During closed chest mitral valve replacement surgery, which is described below, the knot pusher 11 is properly aligned when the major axis of the knot pushing head 13 is tangential to the suture ring of the replacement valve. The round headed knot pushers of the prior art do not have easily visible landmarks on the head to help align them for proper tightening of the knot when the knot reaches the surgical site.

FIGS. 4 A–F show the general procedure for tying suture knots with the surgical knot pusher 11 of the present invention. First, the suture material 30 is sewn with the desired stitch pattern through the tissue or the material that the surgeon wishes to suture. The two ends 31, 32 of the suture must be long enough to extend from the surgical site to beyond the point of entry on the exterior of the body so that the knots can be formed extracorporeally. One end 32 of the suture material 30 is threaded through the single eyelet 18. This can be done with or without the suture needle still attached to the end 32 of the suture 30. The free end 31 of the suture material is "thrown" around the standing end 32 of the suture which passes through the eyelet 18. If a surgeons' knot is desired, two wraps of the free end 31 are thrown around the standing end 32 of the suture 30. The knot pushing head 13 is advanced up to the knot 33 and the free end 31 of the suture is placed in the groove 19 opposite the eyelet 18. A gentle, even tension is exerted on the two ends 31, 32 of the suture 30 to keep them straight and the knot pusher 11 is advanced distally until the knot 33 has been pushed all the way against the tissue being sutured.

Next, the head 13 of the knot pusher is withdrawn to the point of entry and a second throw of the free end 31 of the suture is made around the standing end 32. Typically, a single wrap 34 is thrown in the opposite sense from the previous thrown so that a square knot or reef knot 35 is formed. This second throw 34 of the knot is advanced in the same way as the first throw until it is against the first throw 33 of the knot 35. The knot 35 can be tightened by holding the knot pushing surface 15 against the knot 35 while gently and evenly pulling on the two ends 31, 32 of the suture material. A series of square knots can be added to lock the suture in place by repeating the previously described procedure, alternating the direction of the knot thrown each time.

This throw-and-push, throw-and-push procedure very closely mimics the standard bimanual technique that is used for forming surgical knots in sutures, the only difference being that the knot is pushed forward by the knot pushing device 11 instead of the surgeon's fingertip. Thus, the technique is very easy for the surgeon to learn and it can be done almost as rapidly as the standard bimanual knot tying technique. It should be noted that a lot of time is saved because the free end 31 of the suture does not have to be threaded through an eyelet each time a new throw is added to the knot being tied. This is especially important in the procedure of mitral valve replacement surgery because the 10 to 20 individual sutures are typically tied with 4 to 5 throws per suture.

In the unlikely event that the free end 31 of the suture slips out of the groove 19 on the knot pushing head 13 because of uneven tension applied or because an obstruction interfered with advancing the knot 33, the knot 33 may be temporarily dropped, but it is not lost because the standing end 32 of the suture 30 is always contained by the eyelet 18. The knot pusher 11 does not have to be withdrawn completely to pick up the knot, it need only be withdrawn to a point slightly behind the knot 33, then advanced up to the knot 33 while a light, even tension is maintained on the two ends 31, 32 of the suture to align the free end 31 with the groove 19 opposite the eyelet 18. Then, the knot tying procedure is completed as normal.

The knot pushing device and method of the present invention are particularly well adapted for use in closed chest mitral valve replacement surgery. A brief description of the closed chest mitral valve replacement surgery procedure follows. A more complete description of the procedure can be found in co-pending patent application Ser. No. 08/163,241, the complete disclosure of which has been previously incorporated by reference.

Standard mitral valve replacement surgery is an open heart surgical procedure. As is typical in open heart surgery, the chest is opened to expose the heart, usually by a median sternotomy which involves cutting through the patient's sternum or breastbone, then spreading the ribs apart with a mechanical retractor to expose the interior of the chest cavity. This procedure is tremendously traumatic to the patient's body and is responsible for a large portion of the morbidity and delayed recovery time of the patient after open heart surgery. Surprisingly, the actual surgery on the heart to replace the diseased mitral valve causes considerably less trauma and morbidity than the sternotomy to expose the heart. This aspect makes closed chest cardiac surgery a tremendous opportunity for minimally invasive surgical techniques. The possible benefits to the patient from reduced morbidity and scarring and improved recovery time are almost incalculable.

Figure 5:
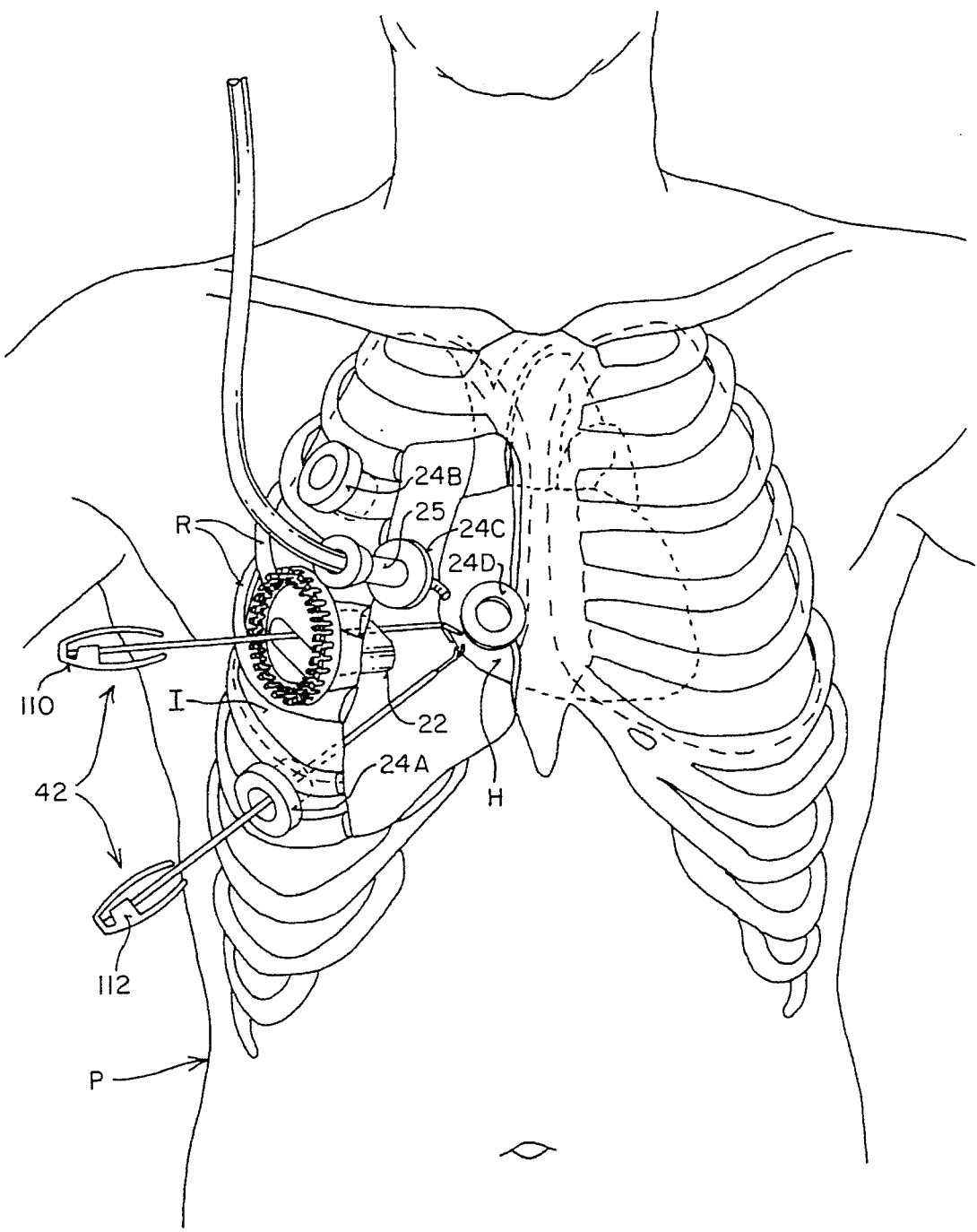
FIG. 5 diagrams the surgical approach used in the closed chest mitral valve replacement surgery.

The surgical approach used in the closed chest mitral valve replacement surgery is shown diagramatically in FIG. 5. To begin the closed chest mitral valve replacement procedure, access to the heart is made through a much smaller lateral incision on the right side of the chest, usually between the fourth and fifth ribs R. A specially designed oval-shaped cannula 22 is placed between the ribs R. The oval shape of the cannula 22 allows the cannula to fit between the ribs with little or no retraction required. Additional access ports 24 A–D are positioned between the ribs at different locations on the right side of the chest for insertion of an endoscope 25 and for retractors and other instruments 110, 112. While viewing the surgical site through the endoscope 25 and by direct visualization through the oval cannula 22, the heart H is located using instruments inserted through the oval cannula 22 and other access ports 24 A–D, and the pericardium is cut open to expose the left atrium.

Figure 6:
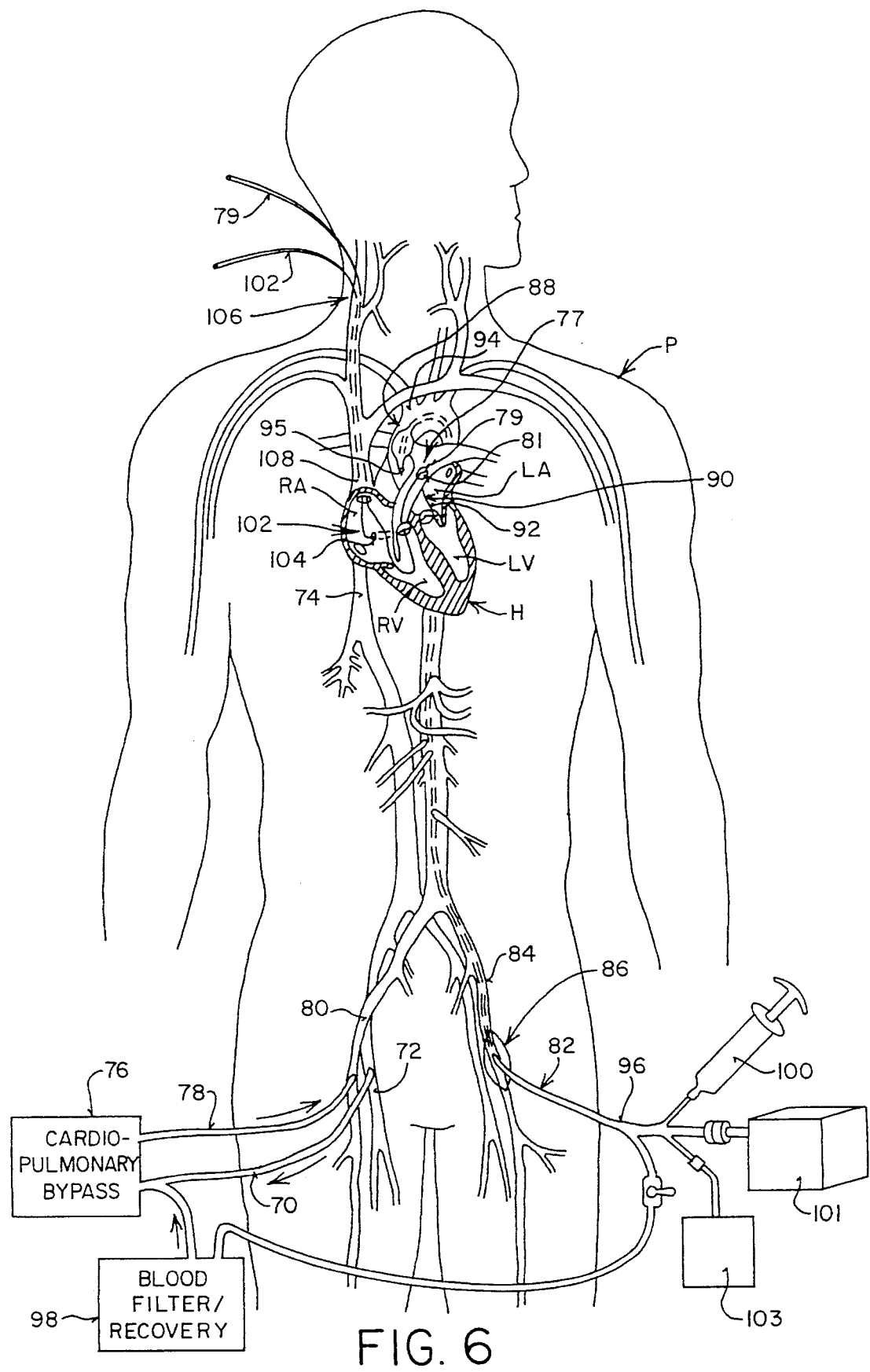
FIG. 6 diagrams the placement of catheters for cardiopulmonary bypass and for administration of cardioplegia in the closed chest mitral valve replacement surgery.

Meanwhile, the femoral artery 80 and the femoral vein 72 are cannulated for connection to the cardiopulmonary bypass machine 76. This step is shown diagramatically in FIG. 6. A specialized catheter 82 is inserted into the opposite femoral artery 84 and is advanced from the insertion site into the ascending aorta. A balloon cuff 88 on the end of the catheter 82 is then inflated to seal off the aorta. The balloon cuff 88 serves the same purpose as cross clamping the aorta during open heart surgery. It also allows the catheter 82 to be used for pumping of protective cardioplegic solution into the coronary arteries through a lumen in the catheter leading to a port 95 in its distal end, thereby perfusing the myocardium to stop the heart. A second catheter 102 may be placed in the coronary sinus to allow retrograde perfusion of cardioplegic solution through the coronary sinus. Another catheter 79 is placed in the pulmonary artery to vent blood and other fluids from the heart. A more complete description of this procedure can be found in co-pending patent applications Ser. No. 07/991,188, filed Dec. 15, 1992 and Ser. No. 08/123,411, filed Sept. 17, 1993, the complete disclosures of which are incorporate herein by reference.

Figure 7:
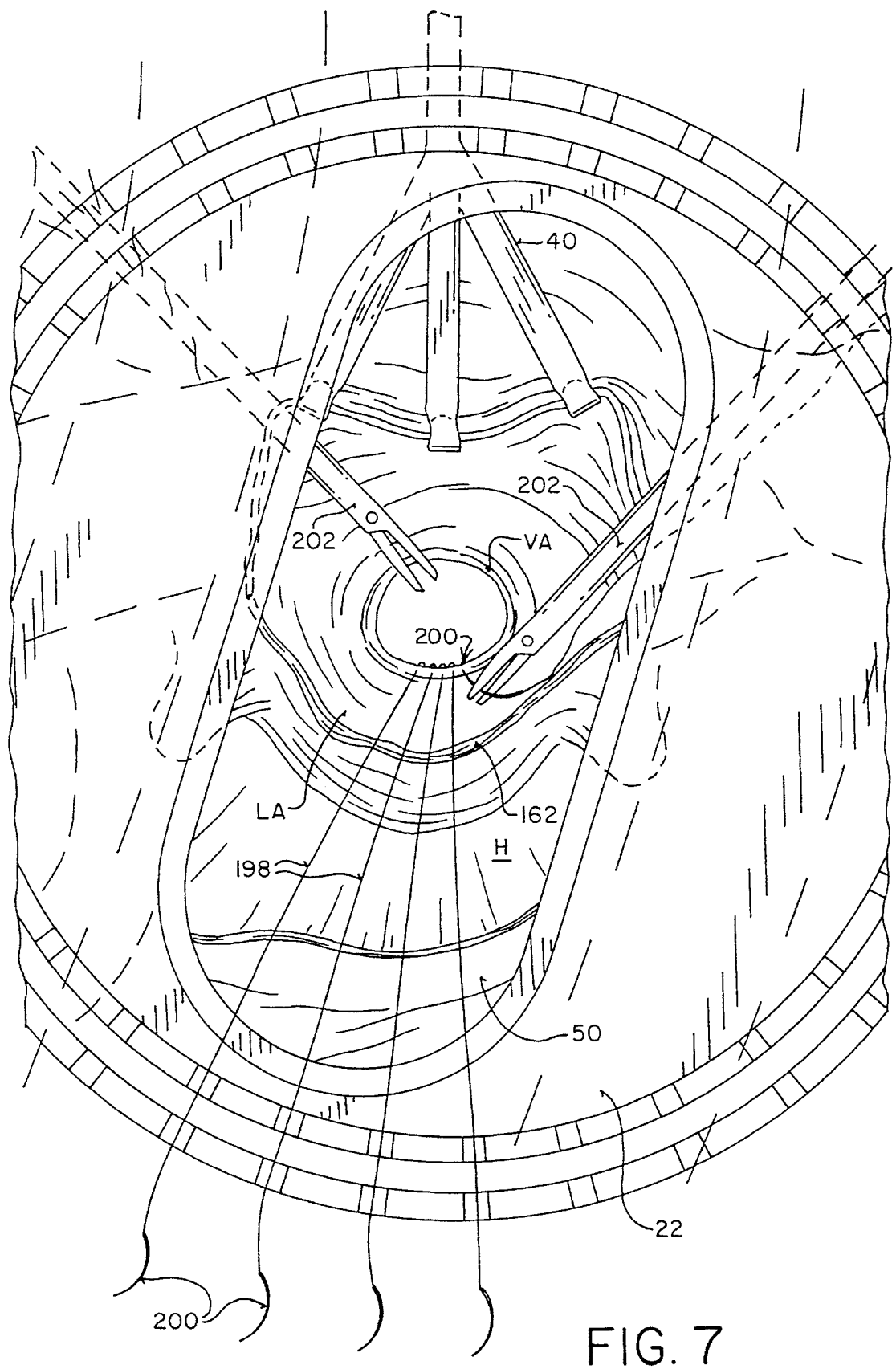
FIG. 7 is a view through the oval cannula showing the sutures being placed in the annulus of the mitral valve.

Referring now to FIG. 7, the left atrium 162 is then cut open to expose the diseased mitral valve, using a cutting instrument introduced through the oval cannula 22 or another access port. The blood is suctioned and flushed out of the left atrium 162 and the pericardium to allow a clear view of the surgical site and to prevent any coagulation of the standing blood. A retractor 40 inserted by way of an access port in the anterior chest wall is used to hold open the incision into the left atrium 162. One at a time, the leaflets of the diseased mitral valve are grasped with forceps and excised with scissors and the chordæ tendineæ connecting the valve leaflets to the papillary muscles are cut so that the leaflets can be removed. The annulus VA of the mitral valve is carefully left intact so that the replacement valve can be sewn to the annulus VA. The size of the annulus VA is measured to estimate the proper size of replacement valve 36 to be used. FIG. 7 shows the view of the heart through the oval cannula 22 after the leaflets of the diseased mitral valve have been excised.

In some cases, it may be preferable to leave the native mitral valve intact instead of excising the leaflets of the valve, particularly when the native mitral valve is insufficient, but not stenotic. This has several potential benefits. It assures that the annulus of the valve is left intact and is not compromised by cutting too close while excising the leaflets of the valve. It also allows the surgeon to leave the chordæ tendineæ and the papillary muscles intact and attached to the cusps of the valve, as it has been found that these tissues add support to the structure of the left ventricle, helping to prevent distention of that chamber. There are also other important vascular and nerve structures that are very close to the annulus of the mitral valve that could be compromised if the surgeon cuts too deeply in removing the leaflets of the valve.

Next, a series of 10 to 20 interrupted horizontal mattress sutures are placed around the circumference of the native valve annulus VA, using 36 inch long 2-0 braided nylon or dacron sutures, or other suitable suture materials, with curved suture needles on both ends 200 of the suture material 198. Endoscopic needle holders 202 are used to introduce the sutures 198 through the oval cannula 22 and drive them through the valve annulus VA, as shown in FIG. 7. Both ends of the sutures 198 are brought out of the body through the cannula 22 and carefully organized around the incision site exterior to the body cavity. Using sutures 198 of alternating colors helps to keep the sutures organized to prevent inadvertent tangling of the sutures.

Once all of the sutures 198 have been placed through the valve annulus VA, both ends of each of the sutures are passed through the sewing ring 228 of the valve prosthesis 36 outside of the chest cavity. The valve prosthesis is then inserted through the oval cannula using a valve holder having an elongated handle. As the valve prosthesis 36 is slid along the sutures 198 into the left atrium, the sutures 198 must be kept in tension and carefully separated. A specialized suture retaining ring may be mounted exterior to the body for this purpose.

Figure 8:
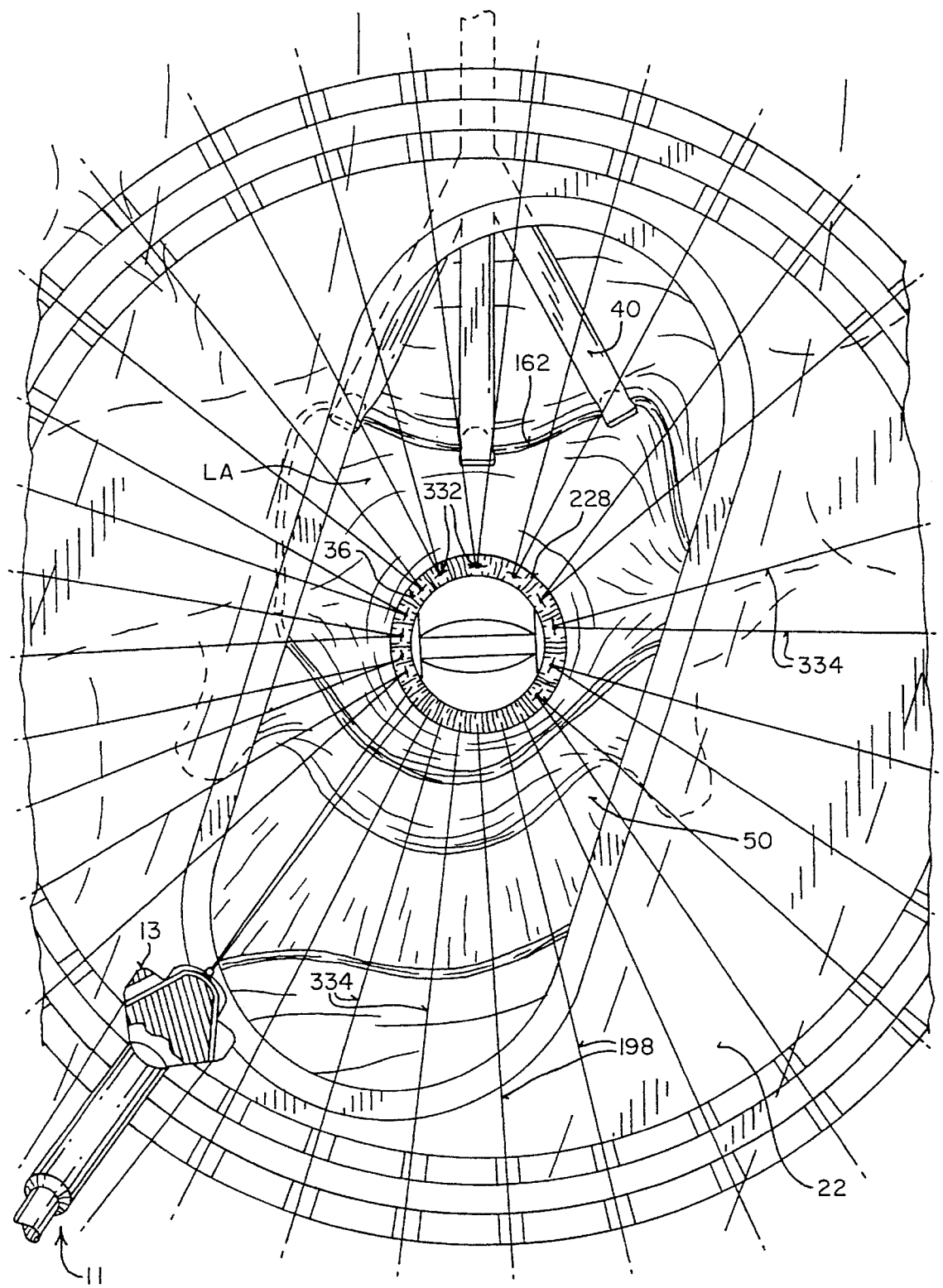
FIG. 8 shows the surgical knot pusher advancing a knot through the oval cannula to secure the replacement mitral valve into the annulus of the valve.
Figure 9:
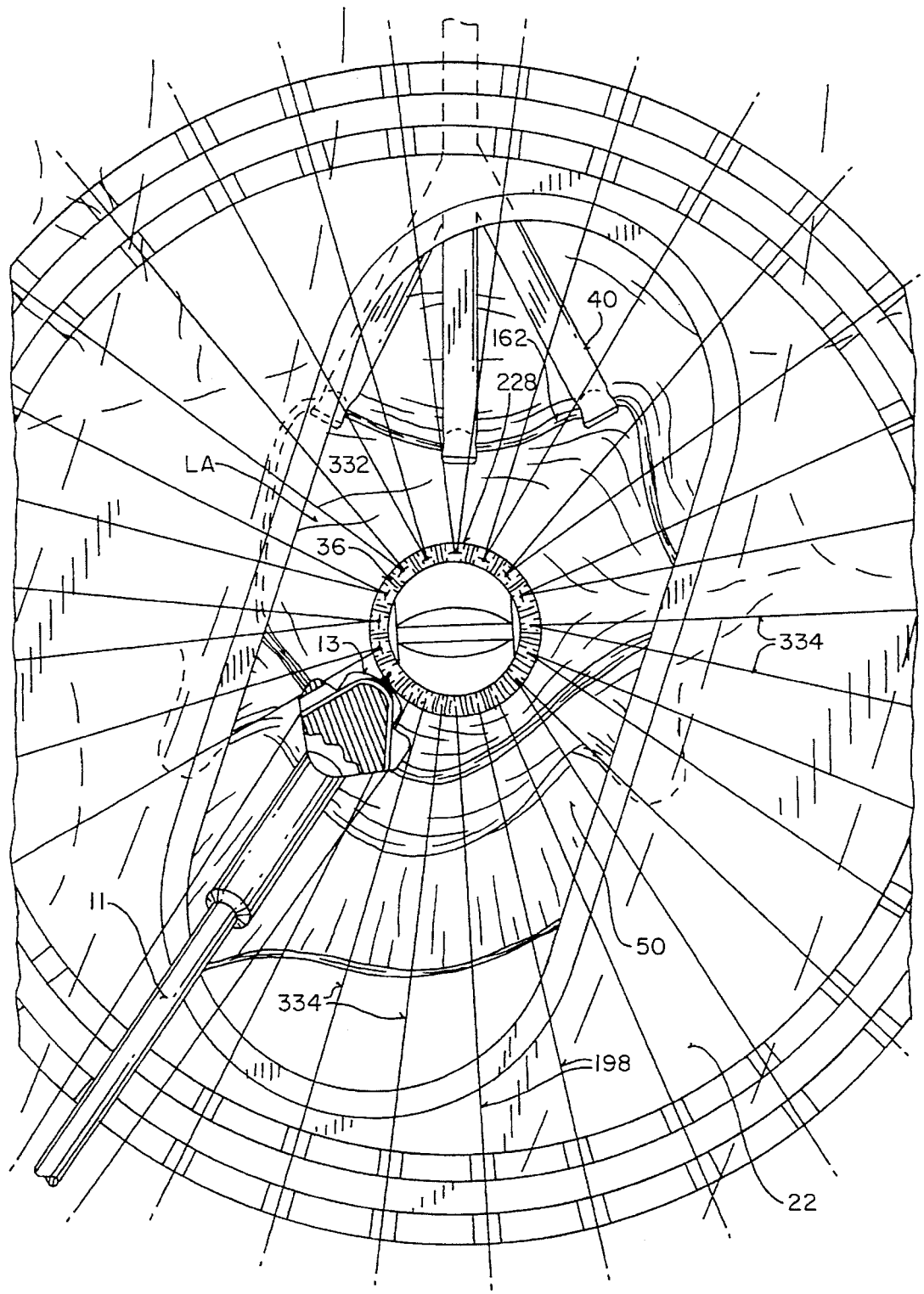
FIG. 9 shows a second knot being advanced through the oval cannula to form a square knot in the suture.
Figure 10:
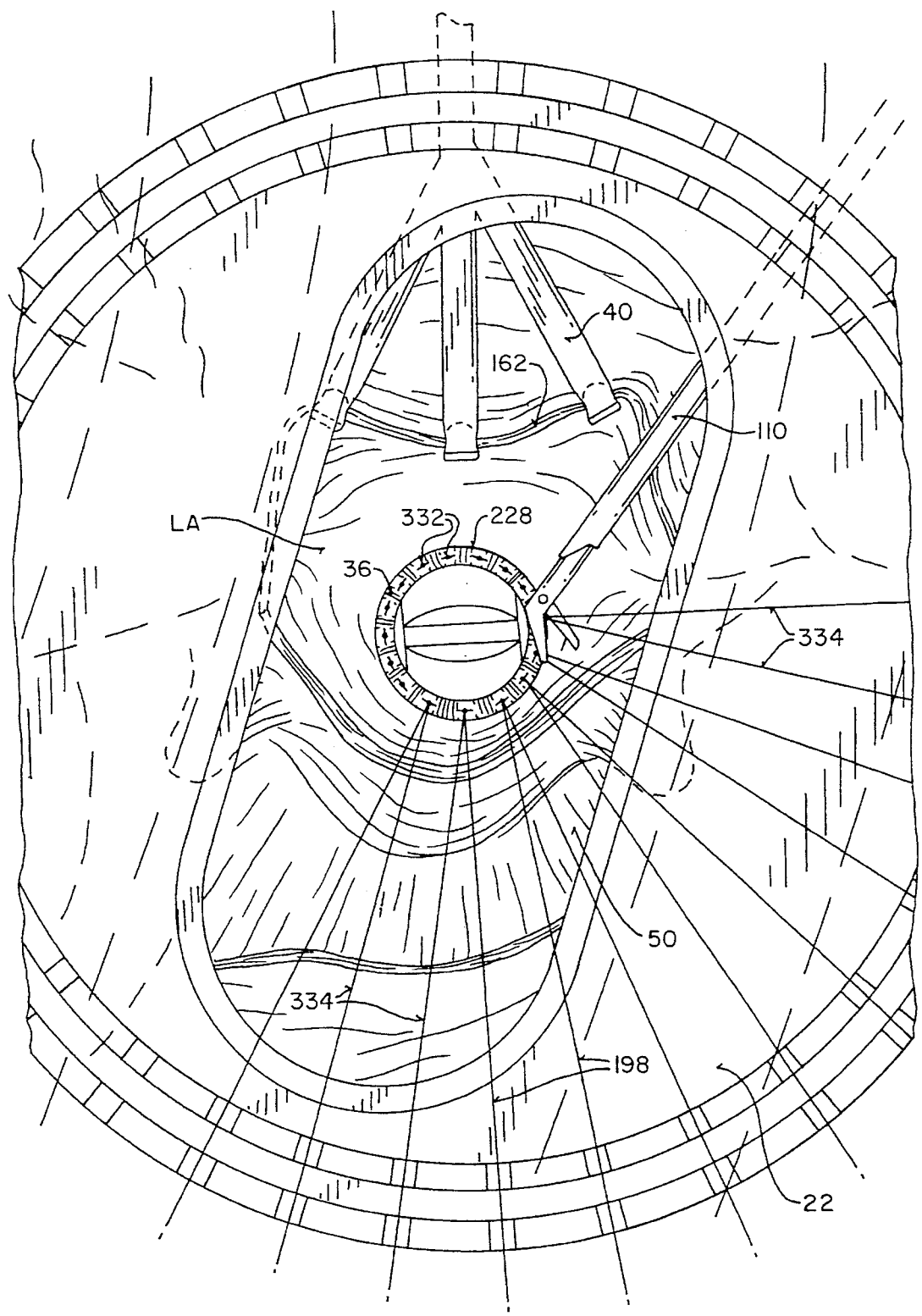
FIG. 10 shows the ends of a suture being cut off to complete the knot tying procedure.

Once the valve prosthesis 36 is seated in the annulus of the mitral valve VA, the surgical knot pusher 11 is used to tie each of the sutures 198 to hold the valve 36 firmly in place and to prevent perivalvar leaks. The two ends 231, 232 of a suture are located and one end 232 of the suture is threaded through the eyelet 18 of the knot pusher 11. The needles 200 may be cut off of the ends of the sutures at this point. The free end 231 of the suture is "thrown" around the standing end 232 of the suture which passes through the eyelet 18 to form an overhand knot 233 and the knot pusher 11 is used to advance the knot 233 along the sutures, as shown in FIG. 8, until the knot 233 is tight against the suture ring 228 of the valve 36. The knot pusher 11 is withdrawn until the head 13 of the device is outside of the body, then a second overhand knot 234 is thrown in the opposite sense to the first knot 233. The second knot 234 is advanced, as shown in FIG. 9, until it is against the first knot 233 so that a square knot 235 is formed. Using this procedure, the sutures are tied with a series of 4 to 5 throws 332. After all of the sutures are tied, the ends of the sutures are cut off with scissors 100 close to the last knot, as shown in FIG. 10. The knot pusher allows quick and efficient tying of the sutures to expedite the procedure as much as possible and reduce the amount of time that the patient has to remain on cardiopulmonary bypass.

Once the valve 36 is sewn into place, the function of the valve is verified and the surgical access can be closed. The atrium is refilled with fluid and all possible air bubbles are vented, then the incision in the atrium is sutured closed, using the surgical knot pusher if desired. The incision in the pericardium is typically not closed, but if desired, may be closed with sutures. At this time, the heart can be restarted, using the procedures described in co-pending patent application, Ser. No. 08/163,241, previously incorporated by reference. The oval cannula is then removed and the chest incision and the additional incisions are closed with sutures or with surgical staples.

Although the examples given include many specificities, they are intended as illustrative of only one possible embodiment of the invention. Other embodiments and modifications will, no doubt, occur to those skilled in the art. For instance, minor variations could be made in the geometry of the knot pushing head while remaining within the spirit and scope of the present invention. Also, while the surgical knot pusher device has been described specifically in relation to the closed chest mitral valve replacement surgery, its usefulness is not limited to this procedure. The device can be used for any number of endoscopic and other minimally invasive surgical procedures, as well as open surgical procedures, with or without modification. Thus, the examples given should only be interpreted as illustrations of some of the preferred embodiments of the invention, and the full scope of the invention should be determined by the appended claims and their legal equivalents.

What is claimed is:

1. A surgical knot pusher, comprising: an elongate shaft having a proximal end and a distal end, a knot pushing surface proximate said distal end, said knot pushing surface defining an arc having a convex curvature, said arc having a first end, a second end and an apex intermediate said first end and said second end, a first suture path extending along said arc from said apex to said first end and a second suture path extending along said arc from said apex to said second end, said first suture path and said second suture path lie within a groove, said groove being defined by a first wall and a second wall, said first wall and said second wall being approximately parallel to one another, said groove between said first wall and said second wall has a first depth proximate said apex of said arc and a second depth proximate said first end and said second end of said arc, said second depth being greater than said first depth, and an eyelet positioned along said first suture path, said eyelet having an aperture therethrough, said aperture being in alignment with said first suture path.

2. The surgical knot pusher of claim 1 wherein said first suture path and said second suture path are approximately symmetrical with one another about said apex of said arc.

3. The surgical know pusher of claim 1 wherein said groove has a concave arc-shaped curvature in a direction transverse to said groove.

4. The surgical knot pusher of claim 1 wherein said convex curvature of said arc comprises a circular arc.

5. The surgical knot pusher of claim 1 wherein said second suture path is open along said arc from said apex to said second end.

6. A surgical knot pusher, comprising:

an elongate shaft having a proximal end and a distal end, a knot pushing surface proximate said distal end, said knot pushing surface defining an arc having a convex curvature, said arc having a first end, a second end and an apex intermediate said first end and said second end, a first suture path extending along said arc from said apex to said first end and a second suture path extending along said arc from said apex to said second end, and an eyelet positioned along said first suture path, said eyelet having an aperture therethrough, said aperture being in alignment with said first suture path, said convex curvature of said arc including a continuous curve having a circular arc proximate said apex of said arc, a first linear extension extending tangential from said circular arc to said first end of said arc, and a second linear extension extending tangential from said circular arc to said first end of said arc.

7. The surgical knot pusher of claim 6 wherein said circular arc subtends an angle of approximately 60 degrees centered symmetrically about said apex of said arc.

8. A surgical knot pusher, comprising:

an elongate shaft having a proximal end and a distal end, a knot pushing surface proximate said distal end, said knot pushing surface defining an arc having a convex curvature, said arc having a first end, a second end and an apex intermediate said first end and said second end, a first suture path extending along said arc from said apex to said first end and a second suture path extending along said arc from said apex to said second end, and an eyelet positioned along said first suture path, said eyelet having an aperture therethrough, said aperture being in alignment with said first suture path, wherein said knot pushing surface is located on a knot pushing head attached to said distal end of said elongate shaft, said knot pushing head having a major axis aligned with said first suture path and said second suture path and a minor axis transverse to said first suture path and said second suture path, said knot pushing head being longer in the direction of said major axis than in the direction of said minor axis.

9. A method of tying surgical sutures comprising the steps of:

a) providing a surgical knot pusher, comprising:
an elongate shaft having a proximal end and a distal end,
a knot pushing surface proximate said distal end, said knot pushing surface defining an arc having a convex curvature, said arc having a first end, a second end and an apex intermediate said first end and said second end,
a first suture path extending along said arc from said apex to said first end and a second suture path extending along said arc from said apex to said second end, said second suture path being open along said arc from said apex to said second end,
and an eyelet positioned along said first suture path, said eyelet having an aperture therethrough, said aperture being in alignment with said first suture path, b) placing a surgical suture through an article to be sutured, said surgical suture having a standing end and a free end, c) passing said standing end of said surgical suture through said eyelet of said surgical knot pusher, d) passing said free end of said surgical suture around said standing end of said surgical suture: to form a knot in said suture between said surgical knot pusher and said article to be sutured, e) aligning said free end of said surgical suture with said second suture path of said surgical knot pusher, f) advancing said surgical knot pusher along said surgical suture toward said article to be sutured while maintaining said free end of said surgical suture aligned with said second suture path and maintaining said standing end of said surgical suture within said eyelet until said knot contacts said knot pushing surface proximate said apex of said arc.

10. The method of tying surgical sutures of claim 9 further comprising the steps of:

g) retracting said surgical knot pusher along said surgical suture while maintaining said standing end of said surgical suture within said eyelet, h) passing said free end of said surgical suture around said standing end of said surgical suture to form a second knot in said suture between said surgical knot pusher and said article to be sutured, i) aligning said free end of said surgical suture with said second suture path of said surgical knot pusher, j) advancing said surgical knot pusher along said surgical suture toward said article to be sutured while maintaining said free end of said surgical suture aligned with said second suture path and maintaining said standing end of said surgical suture within said eyelet until said knot contacts said knot pushing surface proximate said apex of said arc.

11. The method of tying surgical sutures of claim 9 further comprising the steps of:

k) applying further tension on said free end and said standing end of said surgical suture, while holding said knot pushing surface against said second knot to tighten said second knot against said knot.

12. The method of tying surgical sutures of claim 9 wherein said article to be sutured is at a surgical site within a body which is accessible through a cannula, said cannula having a distal end located within said body and a proximal end located external to said body, said cannula having an internal lumen sufficient for passage of said surgical knot pusher through said cannula, said surgical suture being placed through said article to be sutured with said free end and said standing end of said surgical suture extending from said article to be sutured through said internal lumen of said cannula from said distal end to said proximal end of said cannula, said knot in said surgical suture being initially formed external to said body, and said knot being advanced by said surgical knot pusher through said internal lumen of said cannula to said article to be sutured.

13. The method of tying surgical sutures of claim 9 wherein step c) comprises the substep of passing a curved suture needle attached to said standing end of said surgical suture through said eyelet of said surgical knot pusher.

14. A method of tying surgical sutures in heart valve replacement surgery comprising the steps of:

a) providing a surgical knot pusher, comprising:
an elongate shaft having a proximal end and a distal end,
a knot pushing surface proximate said distal end, said knot pushing surface defining an arc having a convex curvature, said arc having a first end, a second end and an apex intermediate said first end and said second end,
a first suture path extending along said arc from said apex to said first end and a second suture path extending along said arc from said apex to said second end, said second suture path being open along said arc from said apex to said second end,
and an eyelet positioned along said first suture path, said eyelet having an aperture therethrough, said aperture being in alignment with said first suture path, b) providing a replacement heart valve, said replacement heart valve having a suture ring around said replacement heart valve, c) creating a surgical access to a heart valve within the heart of a patient, said heart valve having an annulus around said heart valve, d) placing at least one surgical suture through said annulus of said heart valve, said surgical suture having a standing end and a free end, e) passing at least one of said standing end or said free end of said surgical suture through said suture ring of said replacement heart valve, f) advancing said replacement heart valve along said surgical suture until said suture ring is in contact with said annulus of said heart valve, g) passing said standing end of said surgical suture through said eyelet of said surgical knot pusher, h) passing said free end of said surgical suture around said standing end of said surgical suture to form a knot in said suture between said surgical knot pusher and said suture ring of said replacement heart valve, i) aligning said free end of said surgical suture with said second suture path of said surgical knot pusher, j) advancing said surgical knot pusher along said surgical suture toward said suture ring of said replacement heart valve while maintaining said free end of said surgical suture aligned with said second suture path and maintaining said standing end of said surgical suture within said eyelet until said knot contacts said knot pushing surface proximate said apex of said arc, k) further advancing said surgical knot pusher along said surgical suture while maintaining said free end of said surgical suture aligned with said second suture path and maintaining said standing end of said surgical suture within said eyelet to advance said knot toward suture ring of said replacement heart valve while keeping an approximately equal tension on said free end and said standing end of said surgical suture to maintain said knot approximately centered on said knot pushing surface.

15. The method of tying surgical sutures of claim 14 further comprising the steps of:

l) retracting said surgical knot pusher along said surgical suture while maintaining said standing end of said surgical suture within said eyelet, m) passing said free end of said surgical suture around said standing end of said surgical suture to form a second knot in said suture between said surgical knot pusher and said suture ring of said replacement heart valve, n) aligning said free end of said surgical suture with said second suture path of said surgical knot pusher, o) advancing said surgical knot pusher along said surgical suture toward said suture ring of said replacement heart valve while maintaining said free end of said surgical suture aligned with said second suture path and maintaining said standing end of said surgical suture within said eyelet until said second knot contacts said knot pushing surface proximate said apex of said arc, p) further advancing said surgical knot pusher along said surgical suture while maintaining said free end of said surgical suture aligned with said second suture path and maintaining said standing end of said surgical suture within said eyelet to advance said second knot toward said suture ring of said replacement heart valve until said second knot contacts said knot, while keeping an approximately equal tension on said free end and said standing end of said surgical suture to maintain said second knot approximately centered on said knot pushing surface.

16. The method of tying surgical sutures of claim 15 further comprising the steps of:

q) applying further tension on said free end and said standing end of said surgical suture, while holding said knot pushing surface against said second knot to tighten said second knot against said knot.

17. A method of tying surgical sutures in closed-chest heart valve replacement surgery comprising the steps of:

a) creating a surgical access passage to the heart of a patient through a small incision in an intercostal space in the chest of the patient;

b) introducing a replacement heart valve into said heart of said patient through said surgical access passage;

c) placing at least one surgical suture through the tissue of said heart and through said replacement heart valve, said at least one surgical suture having a first end and a second end, at least one of said first end and said second end of said surgical suture extending through said surgical access passage to a point external to said chest of said patient;

d) passing said first end of said surgical suture around said second end of said surgical suture to form a knot in said surgical suture;

e) pushing said knot with a surgical knot pusher placed through said surgical access passage to advance said knot along said surgical suture toward said replacement heart valve, thereby securing said replacement heart valve to the tissue of said heart.

18. The method of tying surgical sutures of claim 17 wherein step c) comprises the substep of extending said first end and said second end of said surgical suture through said surgical access passage to a point external to said chest of said patient, and step d) comprises forming said knot in said surgical suture external to said chest of said patient, and step e) comprises pushing said knot through said surgical access passage with said surgical knot pusher to advance said knot along said surgical suture from a point external to said chest of said patient toward said replacement heart valve, thereby securing said replacement heart valve to the tissue of said heart.

19. The method of tying surgical sutures of claim 17 wherein step e) comprises the substep of passing said second end of said surgical suture through an eyelet proximate a distal end of said surgical knot pusher prior to pushing said knot toward said replacement heart valve with said surgical knot pusher.

20. The method of tying surgical sutures of claim 19 wherein step e) further comprises the substep of pushing said knot with a convexly curved arcuate knot pushing surface adjacent said eyelet.

21. The method of tying surgical sutures of claim 19 wherein step e) further comprises the substep of pushing said knot with a convexly curved arcuate knot pushing surface lying within a groove proximate said distal end of said surgical knot pusher, said convexly curved arcuate knot pushing surface defining a first suture path for said first end of said surgical suture and a second suture path for said second end of said surgical suture, said first suture path and said second suture path being positioned approximately symmetrically about a central point on said convexly curved arcuate knot pushing surface, said eyelet being located along said second suture path.

22. A surgical knot pusher, comprising:

an elongate shaft having a proximal end and a distal end, a knot pushing surface proximate said distal end, said knot pushing surface defining an arc having a convex curvature, said arc having a first end, a second end and an apex intermediate said first end and said second end, a first suture path extending along said arc from said apex to said first end and a second suture path extending along said arc from said apex to said second end, and an eyelet positioned along said first suture path, said eyelet having an aperture therethrough, said aperture being in alignment with said first suture path, wherein said eyelet is configured to allow passage of a curved suture needle through said eyelet.

23. A surgical knot pusher, comprising:

an elongate shaft having a proximal end and a distal end, a knot pushing surface proximate said distal end, said knot pushing surface having a first end and a second end, a first suture path extending from said first end of said knot pushing surface, an eyelet positioned along said first suture path, said eyelet having an aperture therethrough, said aperture being in alignment with said first suture path, and a second suture path extending from said second end of said knot pushing surface, said second suture path being open along the length of said second suture path.

24. The surgical knot pusher of claim 23 wherein said knot pushing surface has a convex curvature.

25. The surgical knot pusher of claim 24 wherein said convex curvature of said knot pushing surface comprises a circular arc, said first suture path comprises a first linear extension extending tangentially from said first end of said knot pushing surface, and said second suture path comprises a second linear extension extending tangentially from said second end of said knot pushing surface.

26. The surgical knot pusher of claim 25 wherein said circular arc of said knot pushing surface subtends an angle of approximately 60 degrees.

27. The surgical knot pusher of claim 23 wherein said knot pushing surface and said second suture path lie within a groove, said groove being defined by a first wall and a second wall, said first wall and said second wall being approximately parallel to one another.

28. The surgical knot pusher of claim 27 wherein said groove between said first wall and said second wall has a first depth proximate said knot pushing surface and a second depth along said second suture path, said second depth being greater than said first depth.

29. The surgical knot pusher of claim 23 wherein said knot pushing surface, said first suture path and said second suture path lie within a groove, said groove being defined by a first wall and a second wall, said first wall and said second wall being approximately parallel to one another.

30. The surgical knot pusher of claim 29 wherein said groove between said first wall and said second wall has a first depth proximate said knot pushing surface and a second depth along said first suture path and said second suture path, said second depth being greater than said first depth.

31. The surgical knot pusher of claim 29 wherein said groove has a concave arc-shaped curvature in a direction transverse to said groove.

32. The surgical knot pusher of claim 23 wherein said knot pushing surface is located on a knot pushing head attached to said distal end of said elongate shaft, said knot pushing head having a major axis aligned with said first suture path and said second suture path and a minor axis transverse to said first suture path and said second suture path, said knot pushing head being longer in the direction of said major axis than in the direction of said minor axis.

* * * * *